United States Patent

Payne et al.

[11] Patent Number: 5,843,876
[45] Date of Patent: Dec. 1, 1998

[54] COMPOSITION

[75] Inventors: Richard Payne, Manasquan; AnBen Hwang, Verona; Ravi Subramanyam, Belle Mead, all of N.J.

[73] Assignee: Colgate-Palmolive Co., New York, N.Y.

[21] Appl. No.: 790,637

[22] Filed: Jan. 29, 1997

Related U.S. Application Data

[60] Provisional application No. 60/010,796 Jan. 30, 1996.
[51] Int. Cl.$^6$ .................. C11D 3/20; C11D 9/04
[52] U.S. Cl. .................. 510/152; 510/447; 510/481; 510/505
[58] Field of Search .................. 510/152, 440, 510/451, 481, 505, 447

[56] References Cited

U.S. PATENT DOCUMENTS

| | | | |
|---|---|---|---|
| 3,285,855 | 11/1966 | Dexter et al. | 252/57 |
| 3,644,482 | 2/1972 | Dexter et al. | 260/473 |
| 4,077,911 | 3/1978 | Okumura et al. | 252/500 |
| 4,282,163 | 8/1981 | Suzuki et al. | 260/409 |
| 4,795,797 | 1/1989 | Turczyk et al. | 523/200 |
| 5,204,022 | 4/1993 | Sharma | 252/363.5 |
| 5,219,892 | 6/1993 | Suhoza | 521/107 |
| 5,358,560 | 10/1994 | Hitch et al. | 106/499 |
| 5,496,555 | 3/1996 | Colwell | 424/401 |
| 5,545,340 | 8/1996 | Wahl et al. | 510/517 |
| 5,594,055 | 1/1997 | Young | 524/291 |
| 5,721,205 | 2/1998 | Barnabas et al. | 510/522 |

FOREIGN PATENT DOCUMENTS

| | | |
|---|---|---|
| 661341 a1 | 7/1995 | European Pat. Off. . |
| 19516698 | 11/1996 | Germany . |
| 9323515 | 11/1993 | WIPO . |

OTHER PUBLICATIONS

Irganox 1010 Antioxidant and Thermal Stabilizer, Ciba Geigy; pp. 1–9.

Mitsui Toatsu, Stabilized Method Monoethanolamine Comprise Add Antioxidant Monoethanolamine Solvent Contain Mono Ethanolamine High Deteriorate Resistance Clean Agent, Derwent Abstract, Dec. 19, 1995.

*Primary Examiner*—Paul Lieberman
*Assistant Examiner*—John R. Hardee
*Attorney, Agent, or Firm*—Martin B. Barancik; James M. Serafino

[57] ABSTRACT

A cleansing composition which comprises a cleansing effective amount of a long chain alkyl or alkenyl containing surfactant or mixtures thereof and a color stabilizing effective amount of a compound selected from the group consisting of a.

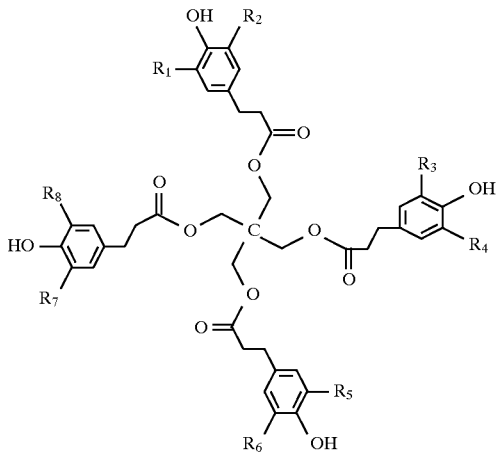

wherein $R_1$, $R_2$, $R_3$, $R_4$, $R_5$, $R_6$, $R_7$ and $R_8$ are the same or different and are isopropyl or tertiary butyl, b.

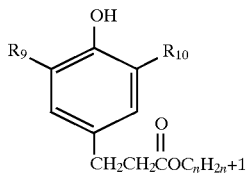

wherein $R_9$ and $R_{10}$ are the same or different and are isopropyl or tertiary butyl and n is about 8 to about 20, or c.

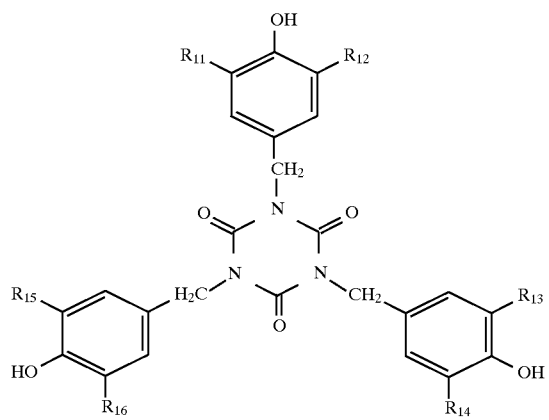

wherein $R_{11}$, $R_{12}$, $R_{13}$, $R_{14}$, $R_{15}$ and $R_{16}$ are the same or different and are isopropyl or tertiary butyl.

24 Claims, No Drawings

COMPOSITION

This application claims the benefit of U.S. Provisional Application No. 60/010,796 filed Jan. 30, 1996.

BACKGROUND OF THE INVENTION

Soap has been used for time memorial to cleanse human skin. Both solid and liquid compositions containing soap have been used to deliver the surfactant to the skin for cleansing purposes. As with virtually every composition used for consumer purposes, the stability of the composition is critical for proper use and/or prolonged storage prior to use.

It is well known that free radical reactions will interfere with the stability of soap containing compositions. Free radicals initiate chain reactions which bring about the deterioration of long chain hydrocarbon materials such as soaps, free fatty acids, synthetic surfactants and the like present in cleansing compositions. Such reactions can bring about among other observable effects, color changes in the cleansing composition and eventually the rancidification of the formulation caused by the presence of breakdown products which are highly odiferous.

The deterioration of the long chain hydrocarbon containing materials can be substantially hindered by the use of known materials to either hinder the catalyzation of certain free radical mechanisms or work as a free radical sink to terminate the free radical chain reaction by rendering the chain free radical harmless. Example of the former type of materials are agents which chelate metals such as copper and iron which are known catalyzers of free radical initiation steps, particularly at points of unsaturation in the hydrocarbon chain. Such agents include ethylene diamine tetra carboxylic acid and its salts and various salts of phosphonic acid derivatives. Exemplary of the free radical sinks are various aromatic compounds which seems to work as a sink for the generated free radials whatever their initial mode of propagation might be. A prime example of this type of compound which has been in use for several decades is butylated hydroxy toluene, (usually known by its abbreviation BHT).

However, even with the use of BHT, stability problems are known to occur. General discoloration of cleansing bars occurs from time-to-time as well as specific points of coloring, usually intensely yellow also occurs. Although unusual, after prolonged periods of time, odors from a soap bar can also occur. Therefore, a need for a better cleansing formulation, particularly solid, stability enhancing additive remains.

SUMMARY OF THE INVENTION

In accordance with the invention, there is a cleansing composition which comprises a cleansing effective amount of a long chain alkyl or alkenyl containing surfactant or mixtures thereof and a color stabilizing effective amount of a compound of the formula selected from the group consisting of

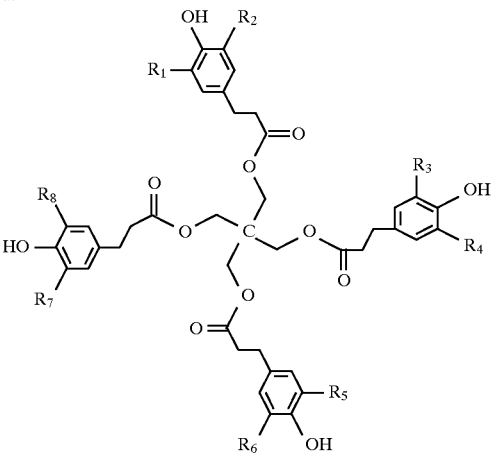

a.

wherein $R_1$, $R_2$, $R_3$, $R_4$, $R_5$, $R_6$, $R_7$ and $R_8$ are the same or different and are isopropyl or tertiary butyl,

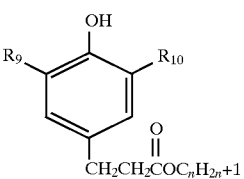

b.

wherein $R_9$ and $R_{10}$ are the same or different and are isopropyl or tertiary butyl and n is about 8 to about 20, or

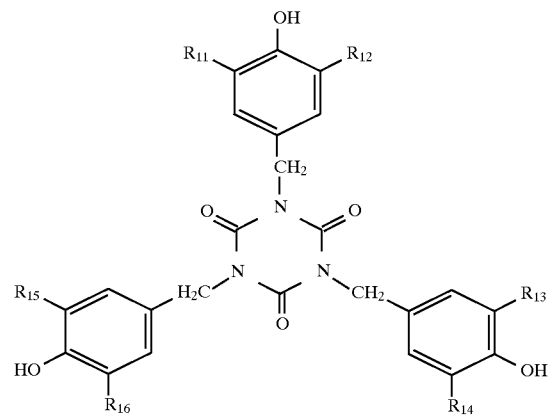

c.

wherein $R_{11}$, $R_{12}$, $R_{13}$, $R_{14}$, $R_{15}$ and $R_{16}$ are the same or different and are isopropyl or tertiary butyl.

A preferred composition is one wherein the surfactant is a soap.

A further preferred composition is a solid, more preferably a bar.

DETAILED DESCRIPTION OF THE INVENTION

Any surfactant may be used in the cleansing composition which removes soil from skin and which is susceptible to degradation upon prolonged shelf-life, particularly with respect to degradation which leads to discoloration and/or unpleasant odors. Therefore, any surfactant which has a long chain alkyl or alkenyl group or mixtures thereof, can be susceptible to such degradation. By long chain is meant at least about 8 carbon atoms, preferably 10, usually normal or having a slight amount of branching. Generally, the maximum number of carbon atoms is not significant but usually above 20 is not preferred. Small quantities of olefinic bond(s) can be present in the predominantly alkyl sections, particularly if the source of the "alkyl" group is obtained from a natural product such as tallow, coconut oil and the like.

Soap, a long chain alkyl or alkenyl, branched or normal carboxylic acid salt such as sodium, potassium, ammonium or substituted ammonium salt can be present in the composition and is preferred.

Examples of such surfactants are the anionic, amphoteric, nonionic and cationic surfactants. Examples of anionic zwitterionic surfactants include but are not limited to alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and the like.

Anionic nonsoap surfactants can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

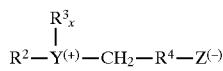

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups.

Examples include: 4-[N,N-di(2-hydroxyethyl)-N-octadecylammonio]-butane-1-carboxylate; 5-[S-3-hydroxypropyl-S-hexadecylsulfonio]-3hydroxypentane-1-sulfate; 3-[P,P-P-diethyl-P3,6,9trioxatetradecyl-phosphonio]-2-hydroxypropane-1-phosphate; 3-[N,N-dipropyl-N-3dodecoxy-2-hydroxypropylammonio]-propane-1-phosphonate; 3-(N,N-di-methyl-N-hexadecylammonio)propane-1-sulfonate; 3-(N,N-dimethyl-N-hexadecylammonio)-2-hydroxypropane-1-sulfonate; 4-(N,N-di(2-hydroxyethyl)-N-(2hydroxydodecyl)ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxylate, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438,091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl)carboxymethyl betaine, oleyl dimethyl gamma-carboxypropyl betaine, lauryl bis-(2-hydro-xypropyl)alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

Many cationic surfactants are known to the art. By way of example, the following may be mentioned:
  stearyldimenthylbenzyl ammonium chloride;
  dodecyltrimethylammonium chloride;
  nonylbenzylethyldimethyl ammonium nitrate;
  tetradecylpyridinium bromide;
  laurylpyridinium chloride;
  cetylpyridinium chloride;
  laurylpyridinium chloride;
  laurylisoquinolium bromide;
  ditallow(Hydrogenated)dimethyl ammonium chloride;
  dilauryldimethyl ammonium chloride; and
  stearalkonium chloride.

Additional cationic surfactants are disclosed in U.S. Pat. No. 4,303,543 see column 4, lines 58 and column 5, lines 1–42, incorporated herein by references. Also see CTFA Cosmetic Ingredient Dictionary, 4th Edition 1991, pages 509–514 for various long chain alkyl cationic surfactants; incorporated herein by references.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

4. Long chain tertiary amine oxides corresponding to the following general formula:

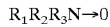

$R_1R_2R_3N \rightarrow 0$ wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and, $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyl-di(2-hydroxyethyl)amine oxide, dimethyloctylamine oxide, dimethyldecylamine oxide, dimethyltetradecylamine oxide, 3,6,9 trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

$RR'R''P \rightarrow 0$ wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecylmethyleth- ylphosphine oxide, 3,6,9-trioxaoctadecyldimethylphosphine oxide, cetyldimethylphosphine oxide, 3-dodecoxy-2-hydroxypropyldi(2-hydroxyethyl)phosphine oxide stearyldimethylphosphine oxide, cetylethyl propylphosphine oxide, oleyldiethylphosphine oxide, dodecyldiethylphosphine oxide, tetradecyldiethylphosphine oxide, dodecyldipropylphosphine oxide, dodecyldi(hydroxymethyl) phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecylmethyl sulfoxide, 3-hydroxytridecyl methyl sulfoxide, 3-hydroxy-4-dodecoxybutyl methyl sulfoxide.

Any quantity of surfactant or mixture of surfactant which brings about a skin cleansing effect can be employed in the composition of this invention. Generally, at least about 1 wt. % of the composition should be surfactant. Preferred minimums of at least about 3, 5, 7, 10, 20 and 30 wt. % surfactant(s) can be present in the composition. Maximum quantities of surfactant(s) depends upon the physical nature of the composition being employed. Generally, no more than about 95–97 wt. % surfactant(s) are present, specifically no more than about 90 wt. % surfactant(s). Maximum quantities of about 20, 30, 40, 50, 60, 70, 80, or 85 wt. % surfactant(s) can also be readily employed.

The anionic surfactant can be present in the composition in various preferred quantities beyond those general quantities previously discussed for all surfactants of from about 1 to about 96 wt. %, specifically about 5 to about 85 wt. %. With respect to liquid, preferably aqueous, compositions, the anionic surfactant(s) is from about 2 to about 20 wt. % of the composition, specifically about 5 to about 15 wt. %. For a solid composition, the anionic surfactant(s) can be from about 5 to about 90 wt. %, preferably from about 10 to about 50 wt. % for a "syndet" bar, about 55 to about 80 wt. % for a "combar", and about 70 to about 90 wt. %, more preferably about 75 to about 85 wt. % in a solid composition wherein there is only one anionic surfactant therein, such as soap.

The antioxidant of the formula is specifically one where all the "R" groups are the same or different and preferably the same in each group a, b or c and most preferably, are all tertiary butyl. When all the "R" groups are tertiary butyl, the compound in group a is available from Ciba-Geigy as Irganox 1010. The CAS number is 6683-19-8 and its chemical name is tetrakis [Methylene (3,5-di-tert-butyl-4-hydroxyhydrocinnamate)] methane. In group b, when the "R" groups are each tertiary butyl and n is 18, the compound is available from Ciba-Geigy as Irganox 1076. The CAS number is 2082-79-3 and its chemical name is octadecyl (3,5-di-tert-butyl-4-hydroxyhydrocinnamate). In group c, when all the "R" groups are tertiary butyl, the compound is available from Ciba-Geigy as Irganox 3114. The CAS number is 2767-62-6 and its chemical name is tris-(3,5-di-tert.butyl-4-hydroxybenzyl)isocyanurate. The quantity of antioxidant percent in the compositions(s) of the invention is an amount effective to provide color stability to the composition upon shelf aging. The upper limit appears to be primarily dependent upon the cost of the material. In solid compositions, generally from about 25 to about 500 ppm of the composition can be employed, preferably from about 50 to about 300 ppm of the composition. In liquid compositions generally from about 10 to about 300 ppm of the antioxidant can be employed, preferably from about 25 to about 250 ppm of the composition.

The physical nature of the composition is not critical and can be a solid, liquid or gel. The method of making such a composition is by the usual methods employed in the detergent industry. The antioxidant is added at the usual point an antioxidant is added in the process.

Below are standard liquid and solid compositions as illustrative examples of the composition(s).

Solid Soap Bar Formula

| Component | % By Weight |
| --- | --- |
| Mixture of Sodium Tallowate, Cocoate, Palmate, and Palm Kernelate soaps | 80–87 |
| Water | 8–10 |
| Glycerine | 0.5–1.5 |
| Fragrance/Dyes | Q.S. |
| Versenex 80-DTPA (40%) | 0.2 |
| Titanium Dioxide | 0.2 |
| Citric Acid (50%) | 0.25 |
| Sodium Chloride | 0.05–1.3 |
| Antioxidant (Irganox 1010 or Irganox 1076 or Irganox 3114) | 0.0025–0.1 |

Liquid

| Component | % By Weight |
| --- | --- |
| Alpha Olefin Sulfonate (40%) | 10.0 |
| Ammonium Lauryl Sulfate (28%) | 25.0 |
| Cocamidopropyl Hydroxy Sultaine (50%) | 3.5 |
| Versene 100 (Dow) EDTA (39%) | 0.2 |
| Propylene Glycol | 1.0 |
| Lauryl diethanolamide | 0.5 |
| Chloroxylenol | 1.0 |
| Citric Acid | Q.S. to pH 5.5–6.5 |
| Fragrance, Dye(s), Preservative | Q.S. |
| Sodium Chloride | 0.05–0.50 |
| Water | 58.5 |
| Antioxidant (Irganox 1010 or Irganox 1076 or Irganox 3114) | 0.001–0.05 |

The compounds of the invention are not restricted to only personal care cleansing compositions. These compounds can also be useful in oral compositions designed for cleansing teeth.

Organic surface-active agents are used in oral compositions to achieve increased prophylactic action, assist in achieving thorough and complete dispersion of any active material such as an anticalculus agent throughout the oral cavity, as well as rendering the compositions more cosmetically acceptable. The organic surface-active material is preferably anionic, nonionic, or ampholytic in nature, and it is preferred to employ as the surface-active agent a detersive material which imparts to the composition detersive and foaming properties. Suitable examples of anionic surfactants are water-soluble salts or higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2 dihydroxy propane sulfonates, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmittoyl sarcosine which should be substantially free from soap or similar higher fatty acid material. The use of such sarcosinate compounds in certain oral compositions is particularly advantageous since these materials exhibit a prolonged and marked effect in the inhibition of acid formation in the oral cavity due to carbohydrate break down in addition to exerting some reduction in the solubility of tooth enamel in acid solutions.

Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoixde (e.g. Pluronic materials).

Generally, surfactants are present in the paste, gel or the typical teeth cleansing composition in from about 1 to about 15 wt % of the composition. The antioxidant of the present invention can also provide stabilization properties to oral compositions containing a peroxide such as hydrogen peroxide or calcium peroxide and the like. The quantity of antioxidant employed is that amount sufficient to stabilize the composition, for example, as a free radical scavenger. Exemplary of such quantities are antioxidant of from about 50 to about 5000 ppm, preferably about 100 to about 2000 ppm of the composition.

The following are examples of the invention which are intended to illustrate the extent of the invention and not be unduly limited thereof.

The following test system was initially employed to evaluate materials which might be stable in an oxidative environment and suitable for preserving cleansing products, particularly soap containing systems.

TEST METHOD

An equal amount of potential antioxidant Irganox 1010 under evaluation and benzoyl peroxide (weight basis) are dissolved into an inert organic solvent such as chloroform to form a 1% (each) solution. 10 ml. of the solution is transferred into a round bottom flask, and heated to boiling under a water cooled condenser. The content is kept refluxing for 15 hours. After removal from heat and allowing to cool to room temperature, the solution is visually inspected for discoloration. This system is designed to bring about yellowing and discoloration which is normally observed in BHT containing cleansing systems.

TEST RESULT

The following materials evaluated show a varied degree of color instability:

Irganox 1010, Irganox 1076 and Irganox 3114 are all more stable than Irganox 1330, which is more stable than Casamine OTB which is more stable than BHT.

a. Irganox 1330 is 1,3,5-trimethyl-2,4,6-tris(3,5-di-tert.butyl-4-hydroxybenzyl)benzene.

b. Casamine OTB is ortho-tolyl biguanide.

The BHT is bright yellow after the test period. The Irganox 1330 and Casamine OTB have varying coloration.

Neither Irganox 1010 nor Irganox 1076 show any discoloration after the test period. Irganox 3114 does not show any significant discoloration after the test period.

A methodology as outlined below was utilized for assessing the color stability of antioxidants in soap formulations.

TEST METHOD 250 ppm each of the antioxidant, Irganox 1010 and benzoyl peroxide and 0.2% $TiO_2$ are homogeneously milled into a soap base. The homogeneous mix is extruded through a plodder to produce a billet which is then pressed in a box shaped die to yield 90 mg. bars. The test bars are rapidly aged in an oven maintained at constant 43 degree C. for 4 weeks, and one bar is retrieved every week to evaluate for color change. The change in color of the soap bars is measured using a reflectance type calorimeter which employs the C.I.E. LAB color space scale (L*a*b*). Where L* indicates the degree of lightness (white, black), a* is the Color Space coordinate defining the red/green and b* is the Color Space coordinate defining the yellow/blue. Freshly prepared bars are pre-read to obtain the initial or standard value. Every seven days bars are read to determine the change in lightness and color. The DL*, Da* and Db* values are the difference in color between the initial and aged samples. The DE* value is a number, calculated from the Color Difference Equation, representing the total color difference (i.e., incorporates lightness and color). Both the Db* and DE* values are monitored to study the color stability of a particular antioxidant in the soap bars. A positive Db* value is indicative of an increase in yellowing, or poor antioxidant color stability. A positive DE* value suggests an increase in the darkness and color of the soap. A more positive value for this measurement indicates a decrease in oxidative stability of the antioxidant.

The Color Difference Equation (DE*) is as follows:

$$DE^* = (DL^{*2} + Db^{*2} + Da^{*2})^{1/2}$$

RESULTS

Irganox 1010 versus the control bar containing BHT show the following trend:

DE*value: Irganox 1010<<<BHT

Db*value: Irganox 1010<<<BHT

Irganox 1010 exhibits good color stability when exposed to strong oxidative environment.

TEST METHOD

Irganox 1010 stability under hydrolytic condition is studied. When boiling as an ethanolic solution in the presence of a strong inorganic base such as sodium hydroxide, Irganox 1010 can be easily hydrolyzed into the corresponding alcohol and carboxylic acid.

Three soap base formulations are prepared to evaluate the hydrolytic stability of Irganox 1010.

(A) Control—Soap chip from typical kettle soap, with 10–13% moisture and 0.02–0.10% free alkalinity as $Na_2O$.

(B) Experiment 1—Addition of 0.25% citric acid to the above soap chips and thoroughly mixing by passing through a laboratory mill.

(C) Experiment 2—Addition of 7% fatty acids blend such as a 50:50 wt. mixture of stearic acid and hydrogenated coco fatty acids to the above soap chips and thoroughly mixing by passing through a laboratory mill.

Irganox 1010 is then intimately blended into each lot of soap at 200 ppm. level. The blends were passed through a laboratory mill repeatedly to insure homogeneity and made into thin ribbons. Each batch of soap ribbon is sealed in three separate glass jars and stored in an oven maintained at 43 degree C. for 4 weeks. Each week, a 2 gram sample of each soap batch is retrieved from the glass jars and analyzed for concentration of Irganox 1010 by an HPLC procedure.

| RESULTS: (Expressed in ppm Irganox 1010) | | | | |
|---|---|---|---|---|
|  | 1 Week | 2 Weeks | 3 Weeks | 4 Weeks |
| Control | 211 | 170 | 130 | 95 |
| Experiment 1 | 212 | 198 | 198 | 182 |
| Experiment 2 | 198 | 182 | 165 | 149 |

The addition of free fatty acid increases the amount of readily oxidizable matter in the system and thereby places an additional stress on the antioxidant. Depending upon the quantities of free fatty acid one employs, it is preferred to use some stronger acid, such as citric, when a free fatty acid is employed.

Irganox 1010 is quite sensitive to soap pH and will maintain its structural integrity only in soaps essentially free of free alkali. A similar issue can present itself with compounds of group b. The excess alkali in soap formulations can be effectively neutralized by the in-situ "superfatting" with strong acids or with free fatty acids. Any quantity of acid which brings about at least essential neutralization of the free alkali can be employed. Quantities of free acid such as citric, acetic, and tartaric as low as about 0.1 wt. % can be employed with effectiveness. The amount of free fatty acid can also vary considerably although generally at least about 3 or 5 wt. % free fatty acid such as stearic, coco, myristic and the like can be employed, preferably at least about 7 wt. % of the composition The final pH of the composition, as measured by 1 wt. % solid composition in water is generally from about 6.5 to about 10.3. Too acidic a pH should be avoided as well since compound cleavage can also occur.

We claim:

1. A solid cleansing composition which comprises at least 30 wt % of a long chain alkyl or alkenyl containing surfactant or mixtures thereof and a color stabilizing effective amount of a compound of from about 10 to about 500 ppm of the composition selected from the group consisting of a.

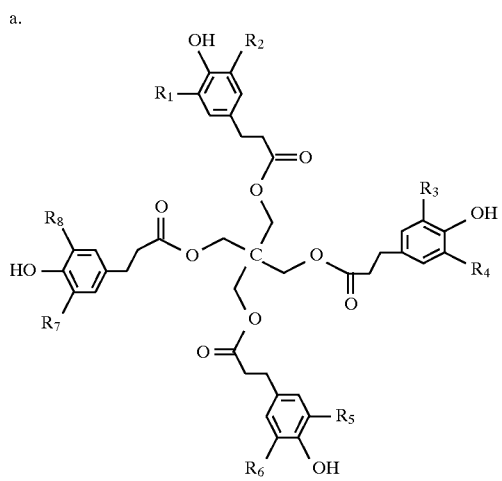

wherein $R_1$, $R_2$, $R_3$, $R_4$, $R_5$, $R_6$, $R_7$ and $R_8$ are the same or different and are isopropyl or tertiary butyl, with the proviso that at least 30 wt % of the composition is an anionic surfactant.

2. The composition in accordance with claim 1 wherein each R in each group a is the same.

3. The composition in accordance with claim 2 wherein each R group is tertiary butyl.

4. The composition in accordance with claim 3 wherein the solid can be hand held.

5. The composition in accordance with claim 4 wherein the solid is in a bar shape.

6. The composition in accordance with claim 3 wherein the compound is present in the composition in from about 25 to about 500 ppm of the composition.

7. The composition in accordance with claim 6 wherein the compound is present in the composition in from about 50 to 300 ppm.

8. The composition in accordance with claim 5 wherein the compound is present in from about 50 to about 300 ppm.

9. The composition in accordance with claim 3 wherein essentially all of the free alkali in the composition is neutralized.

10. The composition in accordance with claim 5 wherein essentially all the free alkali in the composition is neutralized.

11. The composition in accordance with claim 3 wherein there is sufficient strong acid, free fatty acid or mixtures thereof to essentially overcome the hydrolytic effects of free alkali on the compound.

12. The composition in accordance with claim 5 wherein there is sufficient strong acid, free fatty acid or mixtures thereof to essentially overcome the hydrolytic effects of free alkali on the compound.

13. The composition in accordance with claim 6 wherein the surfactant is soap.

14. The composition in accordance with claim 13 wherein the compound is present in from about 25 to about 500 ppm of the composition.

15. The composition in accordance with claim 14 wherein there is sufficient acid to essentially neutralize any free alkali present.

16. The composition in accordance with claim 15 herein the pH of the solid, as measured in a 1% solution in water is from about 6.5 to about 10.3.

17. The composition in accordance with claim 13 wherein soap is about 30 to about 90 wt % of the composition.

18. The composition in accordance with claim 17 wherein soap is at least about 70 wt % of the composition.

19. The composition in accordance with claim 18 wherein the compound is about 25 to about 500 ppm of the composition.

20. A method for cleansing the skin which comprises applying the composition of claim 17 to the skin.

21. A method for cleansing the skin which comprises applying to the skin a composition comprising at least 1 wt. % of a long chain alkyl or alkenyl containing surfactant or mixtures thereof and about 10 to about 500 ppm of a compound of the formula:

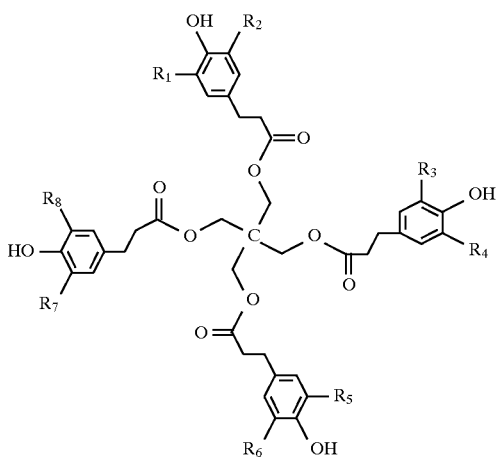

wherein $R_1$, $R_2$, $R_3$, $R_4$, $R_5$, $R_6$, $R_7$ and $R_8$ are the same or different and are isopropyl or tertiary butyl.

22. The method in accordance with claim 21 wherein each R group is the same.

23. The method in accordance with claim 22 wherein each R group is tertiary butyl.

24. A solid cleansing composition which can be hand held and is in a bar shape which comprises at least 1 wt % of a long chain alkyl or alkenyl containing surfactant or mixtures thereof and about 10 to about 500 ppm of a compound of the formula

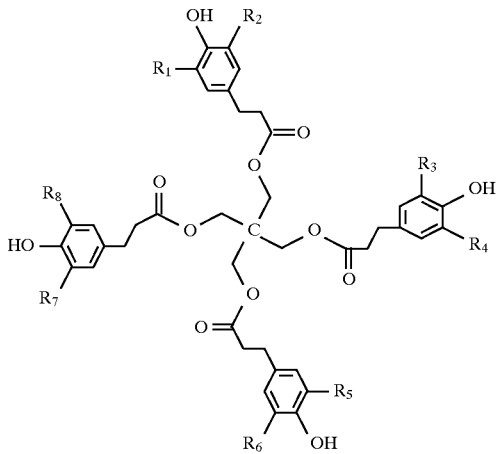

wherein each R group is tertiary butyl and wherein the pH of the bar as measured in a 1% solution in water is about 6.5 to about 10.3.

* * * * *